United States Patent
Thompson (10) Patent No.: US 8,110,186 B2
(45) Date of Patent: *Feb. 7, 2012

(54) METHOD TO MAINTAIN THE EFFICACY OF ORLISTAT

(75) Inventor: Ronald J. Thompson, Fort Thomas, KY (US)

(73) Assignee: Chelatexx, LLC, Fort Thomas, KY (US)

( * ) Notice: Subject to any disclaimer, the term of this patent is extended or adjusted under 35 U.S.C. 154(b) by 122 days.

This patent is subject to a terminal disclaimer.

(21) Appl. No.: 12/658,331

(22) Filed: Feb. 8, 2010

(65) Prior Publication Data

US 2010/0183686 A1     Jul. 22, 2010

Related U.S. Application Data

(60) Continuation-in-part of application No. 11/654,361, filed on Jan. 16, 2007, now Pat. No. 7,662,373, which is a division of application No. 11/522,627, filed on Sep. 18, 2006, now abandoned.

(51) Int. Cl.
*A61K 33/44* (2006.01)
*A61K 9/00* (2006.01)

(52) U.S. Cl. .......... 424/125; 424/400; 514/909
(58) Field of Classification Search .......... None
See application file for complete search history.

(56) References Cited

U.S. PATENT DOCUMENTS

2005/0196374 A1 * 9/2005 Ueda .......... 424/76.1
2009/0068277 A1   3/2009 Park et al.
* cited by examiner

*Primary Examiner* — Qiuwen Mi
(74) *Attorney, Agent, or Firm* — Don Halgren (57) ABSTRACT

A method to effectively treat the adverse events of ingested orlistat, and to maintain the effectiveness of ingested orlistat, the method comprising the steps of: ingesting a compound of orlistat to irreversibly bind with lipase enzymes of the gastrointestinal tract; ingesting a compound of simethicone to cause undigested fats to remain in an emulsified state in the bowel; and ingesting an enteric coated activated charcoal member to absorb emulsified fats only in the lower bowel, thus preventing the adverse events associated with the ingestion of orlistat alone.

11 Claims, 4 Drawing Sheets

The Gastrointestinal Tract

- In response to stomach distension with a meal, the pancreas secretes lipase enzymes into the pancreatic duct, the ampula of vader, and into the duodenum (the initial sgment of the bowel.

- The stomach rhythymcally expells stomach contents into the duodenum to admix with the pancreatic lipase enzyme.

- The pyloric valve prevents backflow reflux

METHOD TO MAINTAIN THE EFFICACY OF ORLISTAT

BACKGROUND OF THE INVENTION

Field of Invention

This invention relates to drugs and medicaments for use in weight loss programs and more particularly for improvements in the use of a pharmaceutical known as orlistat, and is a continuation-in-part application of U.S. patent application Ser. No. 11/654,361, filed Jan. 16, 2007, now U.S. Pat. No. 7,662,373, issued Feb. 16, 2010, which is a division of U.S. patent application Ser. No. 11/522,627, filed Sep. 18, 2006 now abandoned, each of which are incorporated herein by reference in their entirety.

Discussion of Art and Weight Loss Treatments

Orlistat is the generic name of Xenical® (Roche), a prescription lipase inhibitor, FDA approved for weight loss and obesity management in 1999. Lipase is a pancreatic enzyme that breaks down digested fats into small chain fatty acids in the lower lumen of the stomach, and in the small intestine. By inhibiting the actions of the lipase enzyme, ingested fats cannot be absorbed, and weight loss naturally occurs. U.S. Pat. No. 6,607,749 to Daggy, incorporated herein by reference, teaches a dual therapy to treat adiposity with orlistat and to treat the fecal incontinence associated with orlistat, concurrently.

The problem with usage of an orlistat treatment is the undesirable side effects, caused by the passage of undigested fats through the gastrointestinal tract.

Applicants Analysis of the Efficacy & Safety of Weight Loss Drugs Introduction Current medical literature has documented over 400 U.S. deaths directly caused by weight loss drugs. These deaths have been attributed to hemorrhagic strokes, cardiac arrests, and even suicide. In addition, in 1996 it was discovered that the most widely prescribed weight loss drugs had been causing two life threatening conditions: cardiac valve damage and primary pulmonary hypertension. FEN-PHEN/REDUX weight loss regiment had 1.5 million monthly users and generated $3 billion in revenues for Wyeth. However, these specific cardiac and pulmonary diseases related to the aforementioned drugs have caused the pharmaceutical giant to pay over $14 billion in class-action lawsuits.

FEN-PHEN/REDUX are proven weight loss drugs classified as anorectics. Including their generics such as fenfluamine, phenteramine, and dexfenfluamine; all anorectics act as Central Nervous System (CNS=Brain and Spinal Cord) stimulants. It is these sympathlomimetic amines acting as CNS stimulants that have been proven to increase the risk of cardiac valve damage and primary pulmonary hypertension by 23 fold if used for longer than three months.

The Past re Efficacy & Safety of Weight Loss Drugs

In the past 11 years the U.S. Food and Drug Administration (FDA) has mandated that pharmaceutical companies remove numerous weight loss drugs from the market because of deaths and serious complications caused by anorectic weight loss products. All of these CNS stimulating anorectic drugs were FDA-approved and indicated for physician monitored weight loss. With the FDA's primary mission being to assure the U.S. public of the safety and efficacy of drugs, how could this monumental error with anorectics have occurred?

Some of the reasons FEN-PHEN/REDUX and other anorectics were able to pass FDA approval were because of faults in the requirements related to clinical trials. Previous to 1997, CNS stimulant anorectics were only studied for three months at a time and with a limited number of trial subjects (usually less than 2,000). Further, before the FEN-PHEN/REDUX recall the FDA's primary emphasis was on establishing the drug's efficacy for weight loss, not its safety.

Anorectic Weight Loss Drugs Removed from the U.S. Market by the FDA

1973: Amphetamines (All)
    The prototypical anorectic weight loss sympathomimectic amines
    Very effective for appetite suppression and weight loss
    Very addictive
    Meth-amphetamine is the most addictive and widely used illegal drug
    Over-the-counter decongestants were reclassified by the FDA to behind-the-counter drugs to prevent the manufacture of meth-amphetamines
1997: FEN-PHEN/REDUX
    FDA approved as an effective anorectic in 1996
    Linked to over 400 deaths
    Linked to a 23 fold increase in primary pulmonary hypertension and cardiac valve damage if used for more than 3 months
    1.5 million monthly prescriptions of each
    Used by 18 million U.S. citizens
2000: Phenylpropanolamine (PPA)
    Anorectic weight loss sympathomimetic amine
    29 deaths attributed to hemorrhagic stroke
    Mainly in young women
    Usually only after very short term use (6 weeks)
2004: Ephedra (MaHuang) and All Ephedrine alkaloids
    Anorectic sympathomimetic amine
    Sold as a nutritional supplement
    32 deaths caused by myocardial infarction and arrythmias
    Causes seizures
    Causes psychosis
    FDA promptly reclassified Ephedra as an unapproved drug and immediately removed Ephedra from U.S. market
2009: Hydroxycut
    anorectic sympathomemitic amine
    sold as a nutritional supplement—removed from the market on May 1, 2009 by the FDA
    1 death from liver failure
    7 liver transplants for liver failure
    caused jaundice, seizures, cardiovascular disease and rhabdomyolysis
    declared UNSAFE by the FDA

Anorectic

An anorectic is a CNS stimulant, and all anorectics are sympthomimetic amines. These small molecules are rapidly absorbed from the bowel and are completely distributed to all bodily tissues. Sympathomimetic amines include epinephrine (adrenaline), norepinephrine, dopamine, and serotonin. These substance's main function is to mediate the communication between neurons, and are known as neurotransmitters. When a neuron is stimulated, these amines are released from storage vesicles in the distal (far) end of the cell in order to stimulate multiple adjacent neurons. Anorectic agents suppress appetite by stimulating those areas in the brain that tell our stomach it is full.

However, since anorectics are circulated throughout the body, their effects are widespread and include:
- Increased heart rate
- Increased blood pressure
- Increased alertness
- Euphoria (high addiction potential)
- Nervousness and tremors
- Restlessness and agitation
- Insomnia Orlistat, unlike the anorectics is not systematically absorbed, and acts only in the bowel. Orlistat does not stimulate neurons, is not a neurotransmitter, is not a sympathomimetic amine, and is not an anorectic agent. Orlistat is a lipase inhibitor, and generates weight loss by preventing the digestion and absorption on 25-35% of ingested fat. Orlistat, unlike the anorectic, is proven safe.

In November 2008, the FDA DENIED the approval of a new class of weight loss drugs that three major pharmaceutical companies, Sanofi, Pfizer, and Merck had developed. The development and clinical trials of this new class of weight loss drugs cost hundreds of millions of dollars. The new class of weight loss were canniboid-1 receptor antagonists. The FDA denied the approval of these canniboid-1 receptor antagonists because of SAFETY concerns relative to the high incidence of suicide and major psychosis in the clinical trial patients.

Conclusion of Applicants Efficacy & Safety Review

FEN-PHEN was withdrawn from the U.S. market in 1997. Since then, no anorectic drugs have been approved by the FDA because of extreme safety concerns regarding the use of sympathomimetic amine drugs for weight loss. Orlistat, a non systemically absorbed lipase inhibitor was initially FDA-approved as safe and effective in 1999. Further, orlistat's safety was re-affirmed when the FDA allowed it to be converted from prescription status to Over-the-Counter. OTC status confers such a high degree of confidence that a product is safe that a physicians oversight is not even required.

The *Physicians Desk Reference*, incorporated herein by reference, lists the adverse events (side effects) of orlistat clinical trials on over 2800 patients for one or two years as:

Upper gastrointestinal adverse events:

| | |
|---|---|
| Abdominal pain/discomfort | 25.5% |
| Nausea | 8.1% |

Lower gastrointestinal adverse events:

| | |
|---|---|
| Oily Spotting | 26.6% |
| Flatus - with discharge | 23.9% |
| Fecal urgency | 22.1% |
| Fatty/Oily stool | 26.0% |
| Oily Evacuation | 11.9% |
| Increased defecation | 10.8% |
| Fecal incontinence | 7.7% |

Orlistat, as a lipase inhibitor, creates a mal-absorption state, where ingested fats are not absorbed by the intestine, and therefore must be eliminated through the lower intestines and rectum. All of the adverse events are directly caused by the elimination of large sized fat globules.

Table 7.3 of the FDA published "Orlistat Advisory Committee Briefing Document," published in the Federal Register on Jan. 13, 2007 and incorporated herein by reference, documents that 60 mg of orlistat caused adverse events in 89.1% of study participants, and that 120 mg of orlistat caused adverse events in 91.4% of the study participants. The "Orlistat Advisory Committee Briefing Document" also reports that the 60 mg dose of orlistat will prevent the digestion and absorption of 25% of ingested fat. The 120 mg dose of orlistat will prevent the digestion and absorption of 30% ingested fat. The undigested and unabsorbed ingested fats are the etiology of all the adverse events of orlistat use.

The chemical name of orlistat is tetrahydrolipstatin. U.S. Pat. No. 4,598,089 issued Jul. 1, 1986, incorporated herein by reference in its entirety, defines tetrahydrolipstatin, and teaches its unique lipase inhibitor actions. These actions are further defined in U.S. Pat. Nos. 5,245,056 and 5,399,720, (both incorporated herein by reference), to treat obesity and various medical conditions associated with obesity, specifically diabetes and hypertension. U.S. Pat. No. 6,696,467, (incorporated herein by reference) further teaches and defines the specific benefits of the lipase inhibitor tetrahydrolipstatin for the treatment of obesity by weight reduction and appetite suppression. U.S. Pat. No. 6,004,996 (incorporated herein by reference), describes the production of tetrahydrolipstatin into microspheres for the optimal therapeutic delivery into the lumen of the stomach. These microspheres have very efficient action as a lipase inhibitor, because of the large surface area to bind to the lipase inhibitor.

The recent commercial history of orlistat includes the GlaxoSmithKline (GSK) purchase of the United States marketing rights of the orlistat U.S. Pat. No. 4,598,089 from Hoffman la Roche in 2004. The purchase price was one hundred million dollars. GlaxoSmithKline projected yearly revenues of one billion dollars per year from the U.S. sales of the over-the-counter orlistat, marketed by GSK, under the tradename "alli™" for weight loss.

There are two reasons that GlaxoSmithKline confidently projected one billion dollars in yearly over-the-counter orlistat sales: orlistat is the only product that is FDA-approved for weight loss, and obesity is an epidemic/pandemic in the United States. Of the hundreds of products for sale in the United States for weight loss, orlistat is the only product that is FDA-approved for weight loss. This FDA approval is based on a multiple double blind, placebo controlled clinical trial that proved orlistat is effective to induce weight loss. None of the other weight loss products in the documented twenty five billion dollar per year weight loss marketplace, are FDA-approved. The United States Centers For Disease Control (CDC) document that two hundred and forty million U.S. individuals are either over-weight or obese. The U.S. CDC officially claimed that obesity is an epidemic in 2006.

With the overweight/obese potential market of two hundred and forty million individuals, and with the only FDA approved weight loss product for sale in the U.S. market, GlaxoSmithKline confidently projected yearly over-the-counter orlistat revenues of one billion dollars per year.

The actual orlistat sales as reported by GlaxoSmithKline are provided in the chart hereinbelow showing that there is a significant negative impact of orlistat understandably induced by the "adverse events" effects on over-the-counter orlistat sales.

|  | Projected Orlistat Revenues (M) | Reported Orlistat Revenues (M) |
|---|---|---|
| Q2 2007 | 152 | 152 |
| Q3 2007 | 167 | 68 |
| Q4 2007 | 184 | 80 |
| Q1 2008 | 202 | 18 |
| Q2 2008 | 223 | 34 |
| Q3 2008 | 245 | 34 |

* GSK Quarterly Revenue Results Report

Actual over-the-counter orlistat sales have only been a fraction of the projected sales because of the lack of product acceptance by the U.S. public. The lack of product acceptance is because of the socially unacceptable orlistat adverse events of the flatus with discharge and involuntary oily rectal discharge. The orlistat adverse events are reported by over 50% of individuals even on a rigid low fat diet, and over 90% of individuals on a normal (25 grams of fat/meal) US diet, when using orlistat for weight loss.

GlaxoSmithKline employed three actions in their attempt to decrease the impact of the orlistat induced adverse events of flatus with discharge and involuntary oily spotting. Those actions were:
1. Decreasing the recommended dosage of orlistat (alli™)/meal from 120 mg to 60 mg.
2. Marketed to consumers the requirement that they must commit to a low fat diet of no more than 15 grams/meal of fat and be prepared for the orlistat induced adverse events, marketed by GSK as "treatment effects"
3. Attempt to develop a gastrointestinal nuisance controlling agent.

The initial corrective actions of decreasing the orlistat dosage per meal from 120 mg per meal (FDA approved as Xenical in April 1999) to 60 mg per meal, in an failed attempt by GSK, to decrease the orlistat induced adverse events ("treatment effects").

60 mg of orlistat prevents the digestion and absorption of 25 percent of ingested fat, by fecal fat analysis. 120 mg or orlistat prevents the digestion and absorption of 30 percent of ingested fat. The U.S. FDA determined that the 60 mg of orlistat is the minimal effective dose of orlistat that will effect significant weight loss.

The second corrective action employed by GlaxoSmithKline to decrease orlistat included adverse events of flatus with discharge and involuntary rectal spotting was consumer education and marketing. GlaxoSmithKline markets to consumers via advertising and their educational website, www.myalli.com that:
You must commit to a very low fat diet of no more than 15 grams of fat per meal
You may not save fat grams and increase your fat intake at another meal
Wear dark pants to work when you use alli™
Take an extra pair of underwear to work when you are using alli™
Start alli™ on a weekend when you can be home
Experiencing "Treatment Effects" is POSITIVE because it tells you that you have had too much fat in your diet The third corrective action by GlaxoSmithKline was/is to attempt to develop an orlistat induced adverse event controlling agent. GINCA is the acronym for "gastrointestinal nuisance controlling agent". This confirms a 10-year research and development project initiated by Hoffman LaRoche, and continued by GSK, both very skilled in the art, to attempt to develop an antidote or controlling agent to prevent the orlistat adverse events of flatus with discharge and involuntary rectal spotting.

Thus, those skilled in the art thus recognize the failures of everyone to date in overcoming the "adverse effects" of orlistat. The industry is still searching for a solution to the orlistat "treatment effects" to maintain the efficacy of the orlistat treatment dose when multiple drugs are used concurrently. Evidence of this need may be found at: www.innovation.gsk.com, and then search: "wants, healthy living" (item #2), wherein GSK is looking for "a product or formulation that binds the loose fats in the bowel without decreasing the efficacy of orlistat".

The GINCA email cited in U.S. Pat. No. 7,662,373 referenced hereinabove defines steatorrhea as the problem. It is not the problem.

The problem is "Underwear" issues: Not Steatorrhea. Steatorrhea is defined as fatty stools. Steatorrhea is a reported sign of mal-absorption and defines a differential diagnosis of the etiology of the steatorrhea. Individuals experiencing steatorrhea do not experience flatus with discharge or oily spotting (Harrison's Textbook of Internal Medicine, incorporated herein by reference). Orlistat induces a mal-absorption state and therefore will induce steatorrhea, but to convince individuals to maintain a very low fat diet for an extended period of time will probably meet with limited success. I certainly did not become overweight by eating a low fat diet, and I am not committed to maintain a low fat diet just to use orlistat to induce weight loss. Once again, the steatorrhea does not cause the Underwear Issues of flatus with discharge and oily spotting.

Medical Model for "Underwear" Issues

The medical Model for the Underwear Issues of flatus with discharge and oily spotting that negatively impact orlistat product acceptance should be anal incontinence (fecal incontinence) not pancreatic insufficiency or steatorrhea.

Overview of the GI Tract: Anatomy and Physiology

The GI tract is divided into three major areas:
1) Upper GI—mouth, esophagus, stomach
2) Small Intestines—20 ft long, referred to as the 'Bowel' by surgeons
3) Large Intestines—10 ft long, referred to as the 'Colon' by surgeons Though the entire GI tract is comprised of involuntary smooth muscle, there are two areas (upper throat and anal muscles) that also possess voluntary muscle. The mouth and proximal one-third of the esophagus act to allow voluntary swallowing, while the anal apparatus allows for the voluntary release of flatus and defecation. The terminuses of the GI tract are under both voluntary control via striated muscles and involuntary reflex actions on these striated muscles. For example, the 'gag reflex' results due to involuntary reflex action on the proximal striated muscles. 'This gag reflex' can be induced by manually stimulating the posterior pharynx.

The Anal Apparatus

There are two sphincters that control the distal terminus of the GI tract, the internal anal sphincter and the external anal sphincter. The internal anal sphincter is a physiologic sphincter where the terminal sigmoid colon penetrates through a window in the pelvic diaphragm. The pelvic diaphragm is composed of voluntarily controlled striated muscles. By tightening these levator muscles the window is closed via contraction (Kegle exercises). The external anal sphincter is a circular voluntarily controlled striated muscle that acts to maintain closure of the distal terminus of the GI tract. Muscle tone of both sphincters is under autonomic control via the vagus nerve, usually with the external sphincter completely closed and the internal sphincter relaxed. To insure that the sacrospinus nerves are intact, a simple clinical test is employed. The bulbocavernosa reflex is a reflex contracture of external anal sphincter muscle stimulated by the pinching of the clitoris or the glans penis. This reflex arc is involuntary and mediated by the distal spinal cord, just as is the patellar reflex ('knee-jerk' reflex).

The sigmoid colon is filled with sensory proprioceptors that sense pressure. These proprioceptors can usually differentiate the difference between pressure caused by feces in the sigmoid colon and gas in the sigmoid colon. Gas is allowed to escape by the simple voluntary relaxation of the external anal sphincter. Defecation is accomplished by relaxation of the external anal sphincter and increasing intra-abdominal pressure with the abdominal muscles, a voluntary action. The external anal sphincter and the internal anal sphincter are voluntarily contracted when the social situation is inappropriate for the discharge of flatus or feces.

Gas

Gas is produced by normal bacteria that aids in digestion. While this occurs to a small extent in the bowel, it predominantly occurs in the colon, and not at all in the stomach. The gas is propelled along the length of the GI tract by being intermingled with chyme and non-digested, ingested products (like bran) and the normal peristalsis of the smooth muscle. After any abdominal surgery, the bowel peristalsis is paralyzed and the gas accumulates in the bowel and colon. The ability of a post-operative patient to 'pass gas' signals the return of normal peristalsis and bowel function to the surgeon.

In the early 1970's a rectal tube that allows post-operative gas to be relived was introduced, that had an inflatable collar to retain the rectal tube in place. This product was not accepted by patients or surgeons because the inflated collar constantly stimulated the sigmoid colon proprioceptors. This constant stimulation of the sigmoid colon with distending pressure caused a constant sensation of the need to pass gas or defecate.

Understanding Underwear Issues (UI) to Prevent UI Flatus with Discharge (Voluntary Action)

Distension of the terminal sigmoid colon with gas is normal. This distension is perceived by the sensory proprioceptors. Voluntary relaxation of the external anal sphincter allows the gas to escape and relieves the distending pressures on the sigmoid sensory proprioceptors. Large fat globules also, along with gas, can stimulate the sensory proprioceptors. It is this comparable sensory stimulation that can be interpreted as the need to 'pass gas.' This is best described as "playing paintball," a pressurized propellant expelling a semi-solid projectile. To prevent this one can either prevent any large fat globules from presenting to the sigmoid colon (via a low fat diet), or ensure that fat presented to the sigmoid colon is in small droplets or absorbed by activated charcoal. This allows the use of orlistat on a moderate fat diet without the flatus with discharge, because the undigested fat is passed with the stools.

Oily Spotting (Involuntary Action)

Oily spotting is an involuntary reflex of the relaxation of the external anal sphincter in response to fat globule stimulation of the sigmoid sensory proprioceptors. Unlike the bulbocavernosa reflex that contracts the external anal sphincter, oily spotting is caused by the involuntary relaxation of the external anal sphincter much like a gag reflex. Oily spotting usually occurs in the absence of gas, because if sigmoid distending gas were present, either the individual would visit the toilet, or experience the voluntary flatus with discharge. Once again, to prevent oily spotting, prevent large fat globules from stimulating the sigmoid colon sensory proprioceptors. Flatus with discharge and oily spotting are unique to the use of orlistat, not steatorrhea, in individuals with a moderate or high fat ingestion.

BRIEF SUMMARY OF THE INVENTIVE CONCEPTS

The Underwear Issues (UI) of orlistat, flatus with discharge and oily spotting, can be controlled and even prevented by two mechanisms, preventing steatorrhea by ingesting a very low fat diet, or by using a combination of a surfactant like simethicone and fat absorbing activated charcoal. The surfactant used in the upper GI tract insures that the undigested fat remains in a non-globular state so that an oil slick is not presented to the sensory proprioceptors in the sigmoid colon. In addition, the surfactant ensures that the undigested fats are in a small enough droplet state to be absorbed by the activated carbon. By minimizing or preventing the Underwear Issues (UI) related to orlistat use with a moderate fat diet, orlistat can gain better product acceptance. Increased orlistat product acceptance will allow many more individuals to achieve significant long term weight loss.

BRIEF DESCRIPTION OF PRESENT INVENTION

Previous cited patent application Ser. Nos. 11/522,627 and 11/654,361, (now U.S. Pat. No. 7,662,373, both cited hereinabove and incorporated herein by reference) in this series have all defined the use of a surfactant (an emulsifying agent) in the upper gastrointestinal and small intestines to prevent the globulization of orlistat induced undigested, un-dissolved fats. In addition, a chelating agent such as porous activated charcoal, was used in the upper GI (stomach) and the small intestines (bowel). Such applications anticipated the emulsifying agent and chelating agent to be ingested with the orlistat at each meal, and all three dissolved in the stomach and admixed with the stomach contents.

In vitro testing of the orlistat 60 mg and the chelating agent of 400 mg of porous activated charcoal resulted in a 30% decrease in the effective dose of the orlistat. But, the FDA had determined that the minimally effective dose of orlistat to effect clinically significant weight loss was 60 mg. Therefore, to prevent the chelating agent activated charcoal from absorbing orlistat in the stomach, and therefore decreasing the effectiveness of the 60 mg dosage of the orlistat, an enteric coated activated charcoal is now described.

The Encyclopedia of Pharmaceutical Technology, by James Swarbrick and James C. Boylan, incorporated herein by reference, defines enteric coating as a polymer coating for pharmaceutical tablets that prevents the dissolution of the tablet in the stomach and allows the dissolution of the tablet in the small intestines (bowel). This is accomplished by the specific dissolution properties of the enteric film coating, where the coating film is insoluble in the very acidic gastric acid of the stomach (pH 2-2.5) and soluble in the more basic environment of the bowel (pH 5.5-7.5). In fact, the acidity of the contents of the 20 foot long bowel, progressively become less acidic as the contents increase distance from the acidic stomach. This physiologic principle can be used to design an enteric coated tablet that will dissolve at a specific pH in a specific region of the bowel. The enteric film coating is typically 30-50 microns in thickness and referred to as a polymer film coating. Examples of polymer film coating used for enteric coating of pharmaceutical tablets are:

cellulose acetate phthtalate
hydroxy propyl methyl cellulose phthtalate
methylacrylic acid co-polymer type C (USP/NF based)
methylacrylic acid co-polymer type A (USP/NF based)

The enteric coating of pharmaceutical tablets is typically employed in two situations, to prevent the very acidic stomach environment from destroying and therefore decreasing the effectiveness of the ingested medication, and to prevent the ingested medication from eroding or injuring the gastric mucosa. Enteric coatings are widely used in the pharmaceutical industry for these two indications.

The use of enteric coating to prevent drug-drug interactions of multiple concurrently dosed medications in a defined anatomical space, the stomach, is not standard in medicine or the pharmaceutical industry, or anticipated.

The US Centers for Disease Control (CDC) in July 1998, published the FDA recommendations for the treatment options for *Helicobactor pylori* gastric infections. It is "standard of care" in treating gastrointestinal disorders or diseases to concurrently dose several medications. The FDA recommended *H. pylori* treatment options are:

1. Omeprazole 40 mg QD+clarithromycin 500 mg TID×2 weeks, then omeprazole 20 mg QD×2 wks
2. Ranitidine bismuth citrate (RBC) 400 mg BID+clarithromycin 500 mg TID×2 wks, then RBC 400 mg BID×2 wks
3. Bismuth subsalicylate (Pepto Bismol) 525 mg QID metronidazole 250 mg QID+tetracycline 500 mg QID×2 wks+H2 receptor antagonist therapy as directed×4 wks
4. Lansoprazole 30 mg BID+amoxicillin 1 g BID+clarithromycin 500 mg TID×10 days
5. Lansoprazole 30 mg TID+amoxicillin 1 g TID×2 wks
6. Ranridine bismuth citrate 400 mg BID+clarithromycin 500 mg BID×2 wks, then RBC 400 mg BID×2 wks
7. Omeprazole 20 mg BID+clarithromycin 500 mg BID+amoxicillin 1 g BID×10 days
8. Lansoprazole 30 mg BID+clarithromycin 500 mg BID+amoxicillin 1 g BID×10 days The current invention, like the above FDA recommended treatment regimes, utilizes multiple medications dosed concurrently. The use of enteric coated activated charcoal is critical here, concurrently dosed with the orlistat and simethicone, which combination will completely prevent drug-drug interactions between the activated charcoal and the orlistat or the simethicone. This is of critical importance because activated charcoal is indiscriminate and will absorb any medication that it contacts. This is why activated charcoal is indicated in treatment of poisonings. Multiple drug dosing can be used in a single formulation.

The present invention thus includes the use of an emulsifying agent in the stomach and an enteric coated activated charcoal to be ingested together, with the orlistat, which may be formulated into a single capsule or tablet, and still provide sequential actions. None of the three drugs, charcoal, simethicone or orlistat, are systemically absorbed into the body. All three drugs remain in the GI Tract and all are eliminated with defecation.

To understand this, there are three critical facts:
1. Orlistat is dissolved in the stomach and is admixed with all of the stomach's contents from that meal.
2. 90% of the lipase enzyme is from the pancreas, and is not introduced to the stomach's contents until the very first segment of the small intestines, the duodenum. Pancreatic enzymes are secreted by the Ampula of Vader into the small intestines at the duodenum. The pharmacologic action of the orlistat is in the duodenum to bind to the pancreatic lipase enzyme and therefore prevents the pancreatic lipase from digesting the ingested fat.
3. The most critical fact is that the orlistat, once exposed to the pancreatic lipase enzyme in the duodenum, not only inactivates the pancreatic lipase enzyme (25%) but also forms an irreversible bond with pancreatic lipase enzyme.

"Lipstatins an inhibitor of the pancreatic lipase produced by *Streptomyces* Toxytricini." Weibel E K et al. J Antibiotics. 1987 August; 40(8): 1081-5. (incorporated herein by reference).

Dr. Weibel Reports, "Lipstatin contains a beta-lactone structure that probably accounts for the irreversible lipase inhibition."

The significance of this critical fact is that all of the orlistat is irreversibly bound to 25% of the lipase enzymes in the very first 10 centimeters of the small intestines (bowel), the duodenum. By enterically coating the porous activated charcoal, the activated charcoal does not dissolve in the stomach and inactivate the orlistat, but rather dissolves in the mid small intestines after the orlistat has been irreversibly bound to the lipase enzyme. Therefore, by using an enteric coated porous activated charcoal, the small undigested fat, emulsified in the chyme by actions of the emulsifying agent, can be chelated by the released porous activated charcoal in the distal small bowel.

The invention thus comprises the use of an enteric coated, porous, activated charcoal along with the emulsifier simethicone, wherein the orlistat induced "treatment effects" can be controlled. Therefore, the Gastro Intestinal Nuisance Controlling Agent (GINCA) is actually two agents ingested with the orlistat but having their pharmaceutical actions initiated in two different anatomical locations and at two different times. This is a segmental action afforded by the enteric coating of the porous activated charcoal.

BRIEF DESCRIPTION OF THE DRAWINGS

The objects and advantages of the present invention will become more apparent when viewed in conjunction with the following drawings, in which.

DETAILED DESCRIPTION OF THE INVENTION

Figure 1:
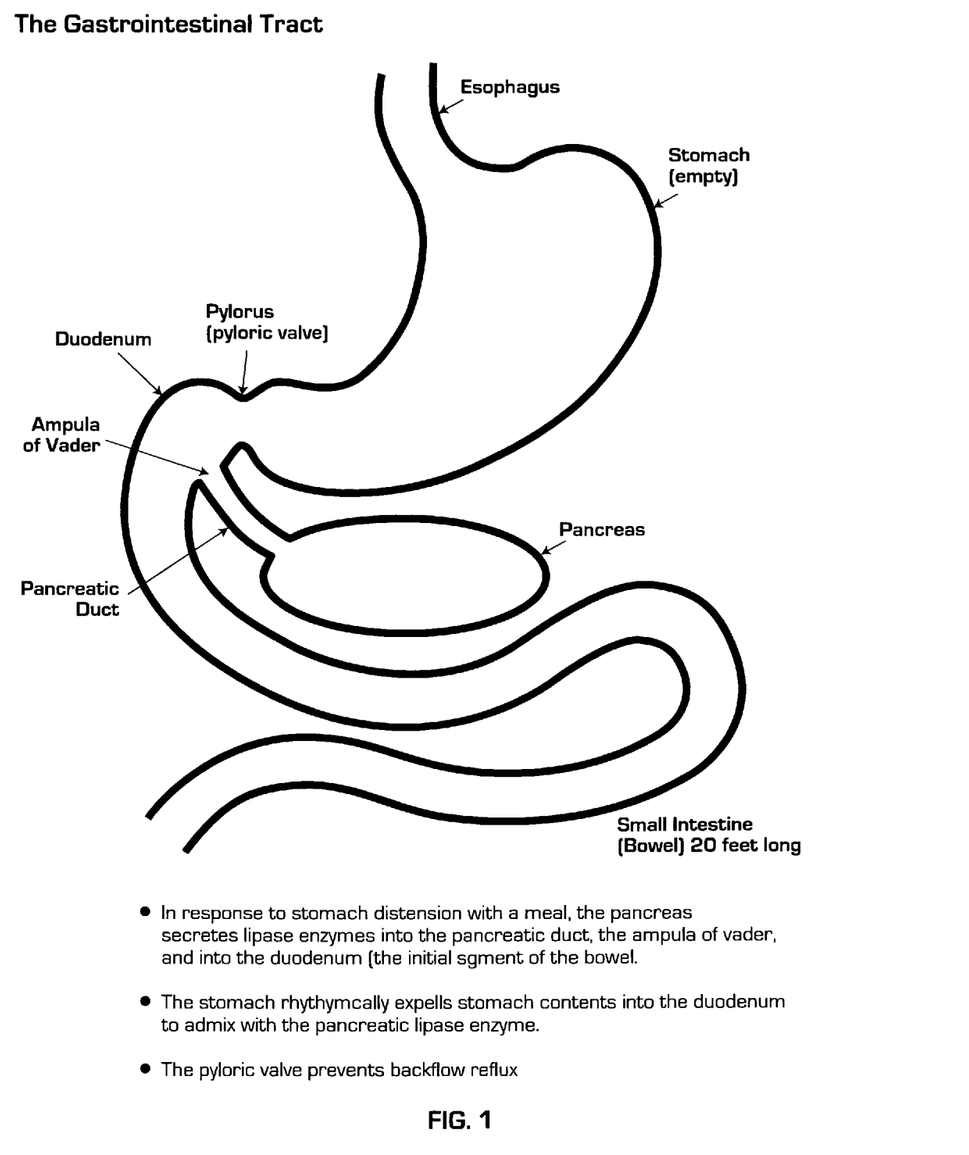
FIG. 1 is a diagrammatic representation, of a human Gastrointestinal Tract, labeled to indicate significant portions thereof.

Referring to the drawings in more detail, FIG. 1 represents a human Gastrointestinal Tract beginning uppermost, with the Esophagus leading to the stomach, shown empty here. The stomach leads to the Pylorus (the pyloric valve) and the Duodenum. The Duodenum is subsequently divided at the Ampula of Vader into the Pancreatic Duct supporting the Pancreas, and into the Small intestine (or lower Bowel, about 20 feet long).

Figure 2:
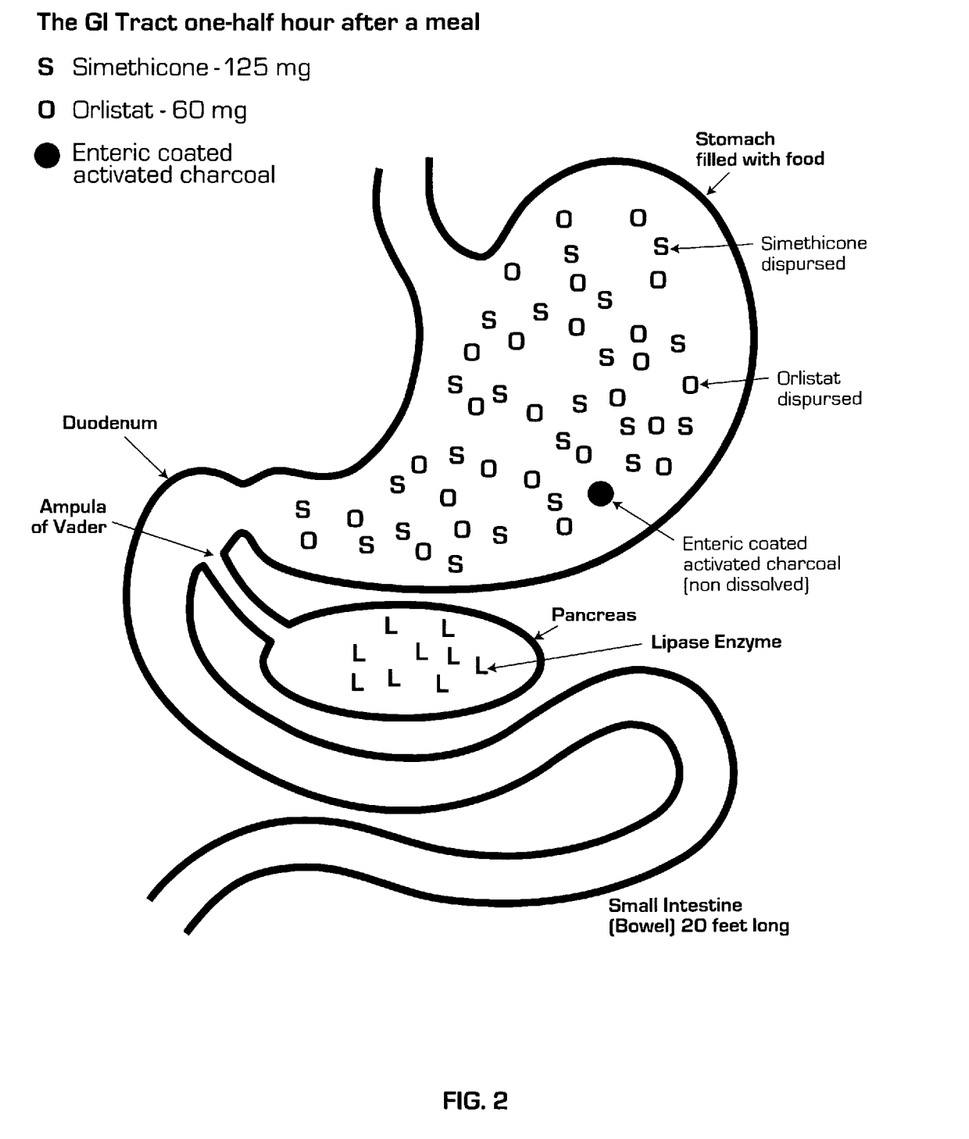
FIG. 2 is a view similar to FIG. 1, showing a Gastrointestinal Tract, with its conditions labeled, represented in about one-half of an hour after a meal has been consumed.

The stomach becomes distended in response to a meal, as represented in FIG. 2, wherein the pancreas secretes lipase enzymes into the pancreatic duct, the ampula of vader and into the duodenum (the initial segment of the bowel). The stomach rhythymically expels the stomach's contents into the duodenum to admix the food with the pancreatic lipase enzyme. The pyloric valve prevents any backflow reflux. In FIG. 2, the distribution of "O's" therein represents orlistat, the distribution of "S's" therein represents for example, about 125 mg of simethicone, the single black dot in the stomach in FIG. 2 represents the enteric coated (non-dissolved) activated charcoal, and the "L's" shown in the pancreas of FIG. 2, represents the lipase enzyme from the pancreas.

Figure 3:
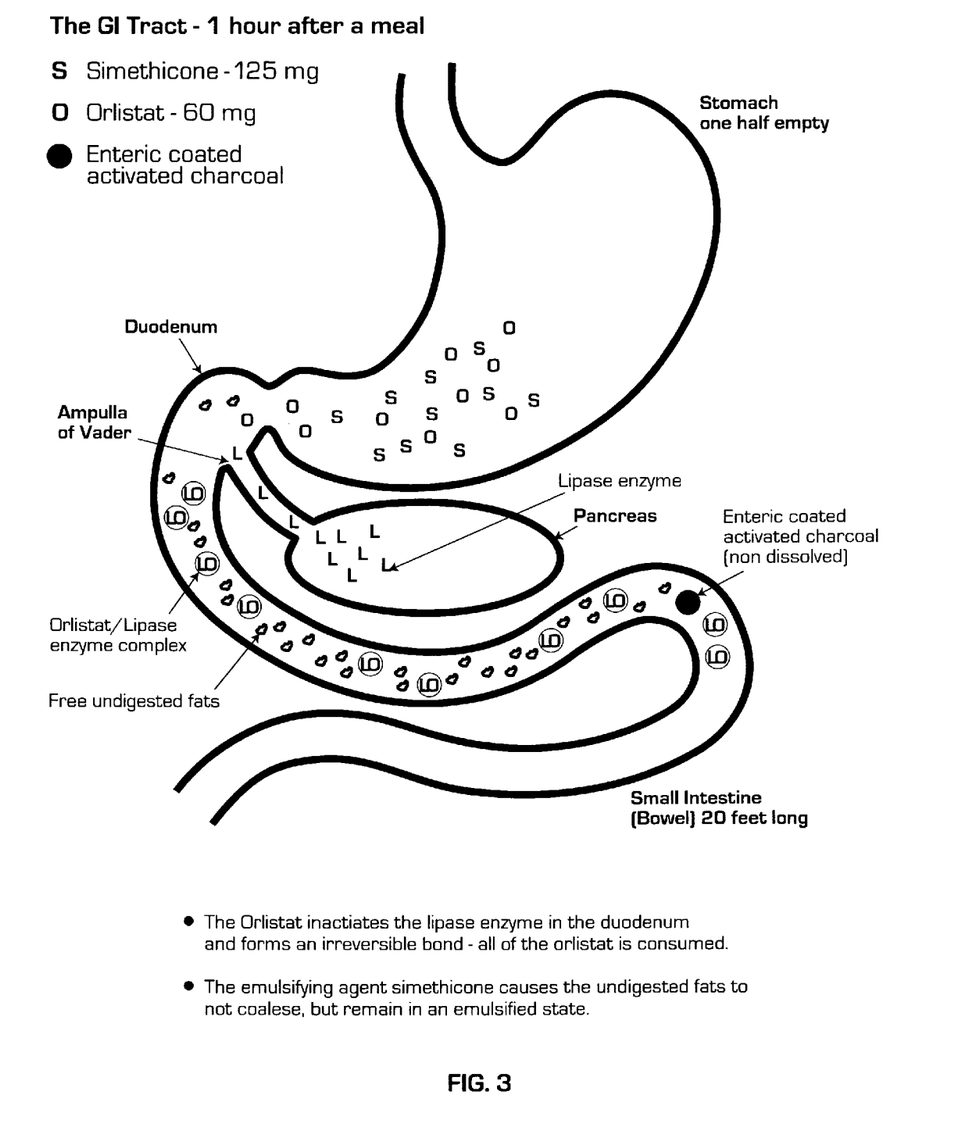
FIG. 3 is a view similar to FIG. 2, showing that Gastrointestinal Tract, with its conditions labeled, represented in about one hour after the meal has been consumed.

FIG. 3 exemplifies the stomach at being about one-half empty, at about one hour after consuming a meal. The lipase has been and is being secreted from the pancreas through the ampula of vader. The orlistat is shown binding with and inactivating the lipase enzyme in the duodenum, forming an irreversible bond therewith, with all of the orlistat being consumed. The emulsifying agent simethicone is shown causing the undigested fates in the bowel to not coalesce, but to remain in an emulsified state. The enteric coated activated charcoal, still not dissolved in the bowel, is shown as the single black dot.

Figure 4:
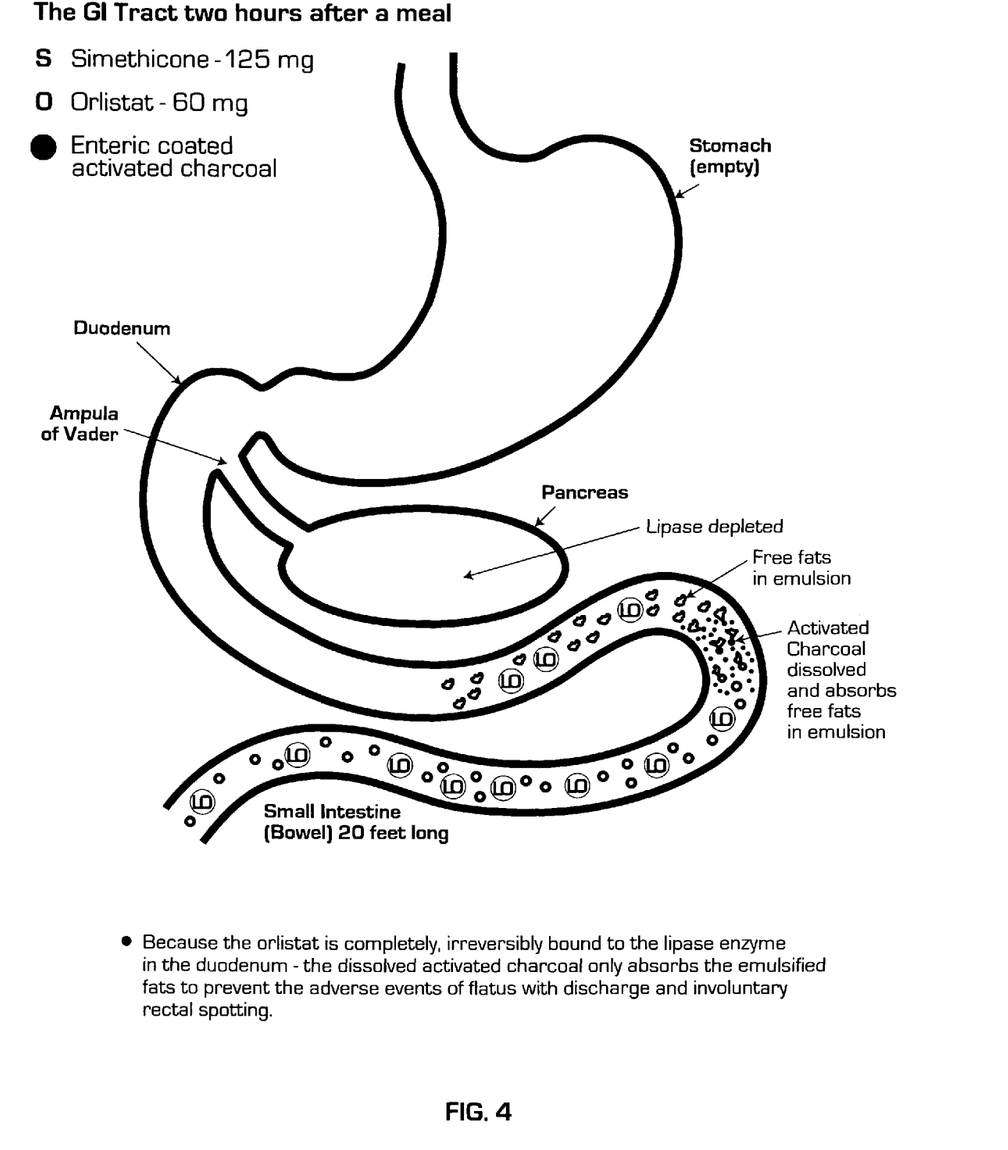
FIG. 4 is a view similar to FIG. 3, showing that Gastrointestinal Tract, with its conditions labeled, represented in about two hours after the meal has been consumed.

FIG. 4 represents the stomach as empty, the pancreas as lipase depleted and free fats in emulsion, the enteric coated activated charcoal now dissolved in the lower bowel, absorbing the free fats in emulsion on their journey through and out the lower intestine. The orlistat is completely irreversibly bound to the lipase enzyme in the duodenum, the dissolved activated charcoal only absorbs the emulsified fates to prevent the "adverse events" of flatus with discharge and the involuntary rectal spotting.

In general terms for the treatment of obesity, orlistat induced weight loss is considered a reversible therapy because the weight loss stops when the user discontinues orlistat therapy. This is compared to non-reversible weight loss therapy from a gastric bypass surgery. In the rationale for using enteric coated activated charcoal that never admixes with or decreases the effectiveness of the orlistat, all of the orlistat is non-reversibly bound to the pancreatic lipase enzyme in the duodenum. Therefore, all of the orlistat is bound and consumed in the first section of the bowel, and the enteric coated charcoal is not released until the mid section of the bowel, which is 10 feet downstream and about one hour later from ingestion. Therefore, by employing enteric coated activated charcoal, ingested concurrently with the orlistat, the two drugs never interface.

Gastrointestinal transit is linear and progressive. As an analogy, it may be compared to two trains traveling from Boston to Miami. The 8 AM breakfast train from Boston, is in NY city at noon, when the noon train leaves Boston bound for Miami. Since both trains use the same tracks (i.e. the GI Tract), and travel at the same speed, they will never collide. This is the linear and progressive normal bowel function that is the rationale for the use of the sequential actions of the orlistat and enteric coated activated charcoal, which prevents the two from ever admixing, even though they are ingested concurrently.

The invention thus comprises a method for the treatment of adverse events associated with the ingestion of orlistat, a lipase inhibitor, consisting of the steps of: ingesting a compound of orlistat, for example, 60 mg or 120 mg of orlistat, a lipase inhibitor; ingesting a compound of simethicone; and ingesting a compound of enteric coated activated charcoal. The simethicone consists of at least about 100 mg to 200 mg thereof per meal. The enteric coated activated charcoal consists of at least about 200 mg to 600 mg thereof, per meal. The compound of simethicone, the compound of enteric coated activated charcoal and the compound of orlistat are ingested individually. The individual ingestion of simethicone, enteric coated activated charcoal and orlistat are taken concurrently.

The invention also comprises a method of delaying the absorption of emulsified fats in the digestive process so as to occur in the lower bowel of the gastrointestinal tract, in order to effectively treat the adverse events of ingested orlistat, and to maintain the effectiveness of ingested orlistat, the method comprising the steps of: ingesting a compound of orlistat to irreversibly bind with lipase enzymes produced in the pancreas of the gastrointestinal tract; ingesting a compound of simethicone to cause undigested fats to remain in an emulsified state in the lower bowel; and ingesting a dose of enteric coated activated charcoal to absorb emulsified fats only in the lower bowel, thus preventing the adverse events of flatus with discharge associated with the ingestion of orlistat alone. The method includes the compound of orlistat, which preferably consists of about 60 mg or 120 mg of orlistat. The method includes the compound of simethicone which preferably consists of for example, about 100 to 200 mg thereof, per meal. The method includes the ingestion of enteric coated charcoal which preferably consists of for example, about at least 200 mg to about 600 mg thereof, per meal.

The invention also includes a method of using only two drugs for the control of the adverse effects of orlistat, an oral lipase inhibitor, without decreasing the safety and the efficacy of the orlistat, the method comprising the steps of: ingesting at least 60 mg or 120 mg of orlistat with a meal; ingesting an enteric coated tablet of at least 200 mg of activated charcoal; and ingesting at least 100 mg of simethicone, concurrently with the ingestion of the orlistat and the enteric coated activated charcoal.

The invention claimed is:

1. A method of concurrently maintaining the efficacy of a specific dose of orlistat and decreasing the adverse events associated with the ingestion of orlistat, a lipase inhibitor, by a subject in need thereof, comprising of the steps of:
   providing a compound of orlistat, a lipase inhibitor, for ingesting by the subject;
   providing a compound of simethicone, for ingesting by the subject; and
   providing a compound of enteric coated activated charcoal, for ingesting by the subject in need thereof.

2. The method as recited in claim 1, wherein the compound of simethicone consists of at least 100 mg thereof.

3. The method as recited in claim 2, wherein the compound of enteric coated activated charcoal consists of at least 200 mg thereof.

4. The method as recited in claim 3, wherein the compound of simethicone, the compound of enteric coated activated charcoal and the compound of orlistat are ingested individually.

5. The method as recited in claim 3, wherein the individual ingestion of simethicone, enteric coated activated charcoal and orlistat are taken concurrently or in a single formulation.

6. A method of delaying the absorption of emulsified fats in the digestive process so as to occur in the lower bowel of the gastrointestinal tract, in order to effectively treat the adverse events of ingested orlistat in a subject in need thereof, and to maintain the effectiveness of ingested orlistat, the method comprising the steps of:

providing an ingestible compound of orlistat to irreversibly bind with lipase enzymes produced in the pancreas of the gastrointestinal tract of the subject;

providing an ingestible compound of simethicone to cause undigested fats to remain in an emulsified state in the lower bowel of the subject; and providing an ingestible enteric coated activated charcoal member to absorb emulsified fats only in the lower bowel of the subject, thus preventing the adverse events associated with the ingestion of orlistat alone.

7. The method as recited in claim 6, wherein the ingestible compound of orlistat consists of 60 mg to 120 mg thereof per meal.

8. The method as recited in claim 7, wherein the ingestible compound of simethicone consists of 100-200 mg thereof per meal.

9. The method as recited in claim 8, wherein the ingestible enteric coated charcoal member consists of at least 200 to 600 mg thereof per meal.

10. The method as recited in claim 8, wherein the ingestible compound of simethicone consists of about 125 mg thereof per meal, and the ingestible enteric coated charcoal consists of about 500 mg thereof per meal.

11. A method of using only two drugs for the control of the adverse effects of orlistat, an oral lipase inhibitor, without decreasing the safety and the efficacy of the orlistat, the method comprising the steps of:

providing at least 60 mg to 120 mg of orlistat for ingestment with a meal;

providing an enteric coated tablet of at least 200 mg of activated charcoal for ingestment with the meal; and providing at least 100 mg of simethicone, concurrently with the ingestion of the orlistat and the enteric coated activated charcoal by a subject in need thereof, for ingestment with a meal.

* * * * *